United States Patent [19]
Yarino et al.

[11] Patent Number: 5,117,015
[45] Date of Patent: May 26, 1992

[54] PROCESS FOR PRODUCTION OF 1-α, 3-β, 24-TRIHYDROXY Δ-5-STEROIDS

[75] Inventors: Tatuo Yarino; Takao Fujii, both of Iwakuni, Japan

[73] Assignee: Teijin Limited, Osaka, Japan

[21] Appl. No.: 696,255

[22] Filed: Apr. 30, 1991

Related U.S. Application Data

[63] Continuation of Ser. No. 374,023, Jun. 30, 1989, abandoned.

[30] Foreign Application Priority Data

Jul. 4, 1988 [JP] Japan .................. 63-165148

[51] Int. Cl.$^5$ .................................... C07J 9/00
[52] U.S. Cl. .................................... 552/541
[58] Field of Search .......................... 552/541

[56] References Cited

U.S. PATENT DOCUMENTS

| | | | |
|---|---|---|---|
| 3,901,928 | 8/1975 | Hesse et al. | 260/397.2 |
| 3,907,843 | 9/1975 | De Luca et al. | 260/397.2 |
| 3,966,777 | 6/1976 | Mazur et al. | 260/397.2 |
| 4,022,891 | 5/1977 | Takeshita et al. | 424/236 |
| 4,305,881 | 12/1981 | Furst et al. | 260/397.2 |
| 4,670,190 | 6/1987 | Hesse et al. | 260/397.2 |

FOREIGN PATENT DOCUMENTS 2400189  7/1975  Fed. Rep. of Germany .
1081424 12/1954  France .

OTHER PUBLICATIONS

Journal of the Chemical Society. Perkin Transactions i, No. 14, Sep. 1975, pp. 1421-1424, Washington, US; M. Morisaki et al.

*Primary Examiner*—Cecilia Shen
*Assistant Examiner*—Jyothsna Venkat
*Attorney, Agent, or Firm*—Sughrue, Mion, Zinn, Macpeak & Seas

[57] ABSTRACT

A process for producing a 1α,3β,24-trihydroxy-Δ$^5$-steroid represented by the formula (II):

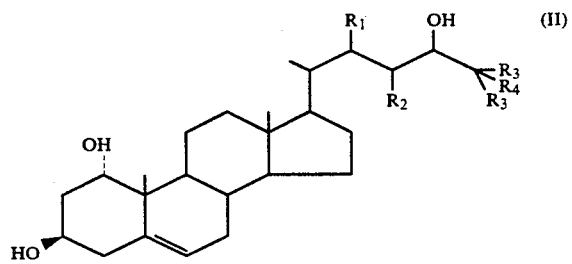

wherein $R_1$ and $R_2$, independently, represent a hyrogen atom, or $R_1$ and $R_2$ together form a single bond, $R_3$ represents an unsubstituted or halogen-substituted lower alkyl, and $R_4$ represents a hydrogen atom, hydroxy or a protected hydroxy, comprising reducing a 1α,2α-epoxy-Δ$^{4,6}$-3,24-dioxosteroid represented by the formula (I)

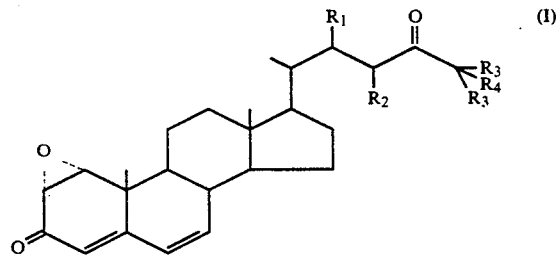

wherein $R_1$, $R_2$, $R_3$ and $R_4$ have the same meanings as defined in formula (II), using an alkaline metal or alkaline earth metal and a proton donor in a solvent comprising ammonia or amine characterized in that at an early stage of the reaction, the 1α,2α-epoxy-Δ$^{4,6}$-3,24-dioxosteroid is reacted with the alkaline metal or alkaline earth metal in the presence of a proton acceptor, and then at a later stage of the reaction, a resulting intermediate product is reacted with the proton donor.

1 Claim, No Drawings

PROCESS FOR PRODUCTION OF 1-α, 3-β, 24-TRIHYDROXY Δ-5-STEROIDS

This is a Continuation of Application No. 07/374,023 filed Jun. 30, 1989 now abandoned.

BACKGROUND OF THE INVENTION

1. Field of the Invention

The present invention relates to a novel process for producing 1α3β, 24-trihydroxy-Δ$^5$-steroid compounds from 1α, 2α-epoxy-Δ$^{4,6}$-3,24-dioxo steroid compounds. The 1α, 3β, 24-trihydroxy-Δ$^5$-steroid compounds are useful for producing 1α, 24-dihydroxy-vitamin D$_3$ derivatives according to, for example, a process described in Japanese Unexamined Patent Publication No. 56-92266. Accordingly, the present process is a unit process in the synthesis of vitamin D$_3$ derivatives.

2. Description of the Related Art

As processes for the production of 1α, 3β, -dihydroxy-Δ$^5$-steroid compounds, Japanese Examined Patent Publication Nos. 53-9222, 53-24073, and 58-54160 disclose processes wherein 1α, 2α-epoxy-Δ$^{4,6}$-3-oxosteroid compounds are reduced by an alkaline metal and a proton donor in a mixed solvent comprising liquid ammonia. But, the application of the conventional processes to the production of 1α, 3β, 24-trihydroxy-Δ$^5$-steroids provides a yield lower than that when applied to the production of 1α, 3β-dihydroxy-Δ$^5$-steroids and therefore, the processes are disadvantageous from an industrial point of view.

SUMMARY OF THE INVENTION

Accordingly, the present invention provides an improved novel process for the production of 1α, 3β, 24-trihydroxy-Δ$^5$-steroids from 1α, 2α-epoxy-Δ$^{4,5}$-3,24-dioxosteroids, which process provides a high yield of the desired compound.

More specifically, the present invention provides a process for production of a 1α, 3β, 24-trihydroxy-Δ$^5$-steroid represented by the formula (II):

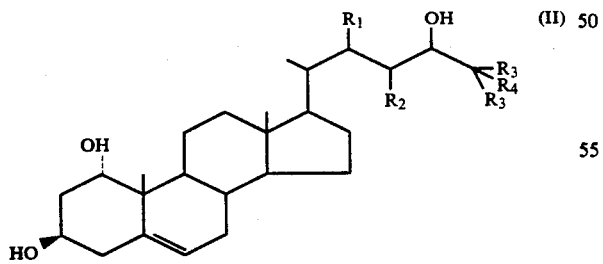
(II)

wherein R$_1$ and R$_2$, independently, represents a hydrogen atom, or R$_1$ and R$_2$ together form a single bond, R$_3$ represents an unsubstituted or halogen-substituted lower alkyl, and R$_4$ represents a hydrogen atom, hydroxy, or a protected hydroxy; comprising reducing a 1α, 2α-epoxy-Δ$^{4,6}$-3,24-dioxosteroid represented by formula (I):

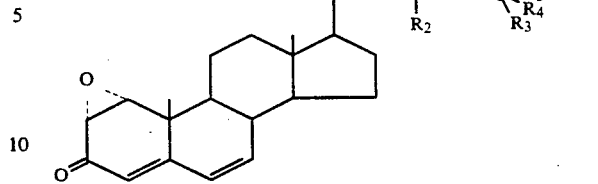
(I)

wherein R$_1$, R$_2$, R$_3$ and R$_4$ have the same meanings as defined in formula (II), using an alkaline metal or alkaline earth metal and a proton donor in a solvent comprising ammonia or amine, characterized in that at an early stage of the reaction, the 1α, 2α-epoxy-Δ$^{4,6}$-3,24-dioxosteroid is reacted with the alkaline metal or alkaline earth metal in the presence of a proton acceptor, and then at a later stage of the reaction, a resulting intermediate product is reacted with the proton donor.

DESCRIPTION OF THE PREFERRED EMBODIMENT

As described above, where a conventional process for producing 1α, 3β-dihydroxy-Δ$^5$-steroid from 1α, 2α-epoxy-Δ$^{4,6}$-3-oxosteroid is applied to the production of 1α, 3β, 24-trihydroxy-Δ$^5$-steroid from 1α, 2α-epoxy-Δ$^{4,6}$-3,24-dioxosteroid, the process provides a low and unsatisfactory yield of the desired steroid. To clarify the reason for the low yield, the present inventor separated and identified a byproduct formed upon reduction of 1α, 2α-epoxy-Δ$^{4,6}$-3,24-dioxosteroid. The byproduct comprised a dimer represented by the formula (III):

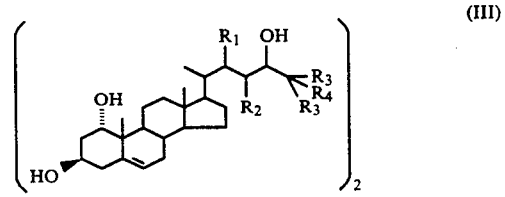
(III)

wherein R$_1$, R$_2$, R$_3$ and R$_4$ have the same meanings as defined in formula (I), resulting in a lowering of the yield. The reduction of 1α, 2α-epoxy-Δ$^{4,6}$-3-oxosteroid does not provide a corresponding dimer.

Generally, to prevent the formation of a dimer, a method is known wherein a reaction is carried out in the presence of a proton donor present from an early stage of the reaction to accelerate reduction of an anion radical to a corresponding alcohol. Nevertheless, application of that method to the reduction of 1α, 2α-epoxy-Δ$^{4,6}$-3,24-dioxosteroids promotes undesirable side reactions, and therefore, the method cannot be applied to the present purpose. The present inventors then, surprisingly, found that formation of a dimer can be prevented by acting a proton acceptor on a keton moiety at the 24 position of a starting steroid at a early stage of the reaction to form an intermediate enol anion which is not reduced and then adding a proton donor at a later stage of the reaction to convert the enol anion to an intermediate keton, which is then reduced to the desired alcohol.

In the above-mentioned formulae (I), (II) and (III), the unsubstituted lower alkyl is a C$_{1-6}$ alkyl, such as methyl, ethyl, n-propyl, isopropyl, n-butyl, isobutyl, tert-butyl, n-pentyl, and branched pentyls, as well as n-hexyl and branched hexyls. Among the above, methyl group is especially preferable. The halogen-substituted lower alkyl as $R_3$ is, for example, $C_{1-6}$ alkyl mono-, di- or tri-substituted with fluorine, clorine or bromine, such as a lower alkyl substituted with fluorine. Especially, the trifluoromethyl group is preferable.

As protecting groups in the protected hydroxy group of $R_4$, there are mentioned acyl radicals derived from aliphatic or aromatic carboxylic acids having 1 to 12 carbon atoms, or nitro-, halogeno- or alkoxy-substituted derivatives thereof, such as acetyl, propanoyl, cyclohexanoyl, chloroacetyl, bromoacetyl, benzoyl, p-bromobenzoyl, p-nitrobenzoyl, ethylbenzoyl and the like, as well as radicals which form an ether bond with a hydroxy group, for example, tert-butyl, benzyl, triarylmethyl such as triphenyl methyl, tetrahydropyranyl, methoxymethyl, alkyl-substituted silyl such as trimethylsilyl and the like. Among the above, acetyl, benzoyl, propanoyl, and the like are preferable.

As a proton acceptor used in the present process, any base having an alkaline strength suitable for the conversion of a ketone to a corresponding enol anion can be used, and a base having an alkaline strength of about pK 16 to 19 is particularly preferable. A base having too high an alkaline strength is not preferable because such a base has a tendency to convert a 5-ene compound to a 4-ene compound. The preferable proton acceptor is an alkaline metal alkoxide, preferably an alkoxide of a primary alcohol with lithium, potassium or sodium, such as lithium ethoxide, potassium ethoxide, sodium ethoxide, lithium propoxide, potassium propoxide, sodium propoxide, lithium n-butoxide, potassium n-butoxide, sodium n-butoxide, or the like.

The amount of proton acceptor added to the reaction is preferably 1 to 30 equivalent amount relative to the amount of starting $1\alpha, 2\alpha$-epoxy-$\Delta^{4,6}$-3,24-dioxosteroid. An amount of less than one equivalent is not effective, and more than 30 equivalents of proton acceptor promotes an isomerization side reaction. Therefore, the use of both too small an amount and too large an amount of proton acceptor is not preferable.

The proton acceptor is preferably added to the reaction mixture prior to addition of the alkaline metal or alkaline earth metal.

The alkaline metal used in the present process is one of lithium, sodium and potassium, preferably lithium. The alkaline earth used in the present process is preferably calcium.

The amount of alkaline metal or alkaline earth metal used is not critical, but is preferably 12 to 90 equivalent, more preferably 25 to 70 equivalent, most preferably 30 to 55 equivalent, relative to the amount of starting $1\alpha, 2\alpha$-epoxy-$\Delta^{4,6}$-3,24-dioxosteroid.

The amines used in the present process are, for example, primary-, secondary- and tertiary-alkylamines, for example, primary lower alkyl amines such as methylamine and ethylamine, di-(lower alkyl)amines, such as dimethylamine and diethylamine, and tri-(lower alkyl)amines such as triethylamine; diamine, for example, lower alkenediamine such as ethylenediamine and propylenediamine; as well as saturated heterocyclic amines such as piperidlne and piperazine.

The solvent used in a mixture with ammonia or amine in the present process is not critical, and is exemplified by an inert organic solvent, such as ethyl ether, tetrahydrofuran, dioxane, hexane or the like.

A concentration of ammonia or amine in a mixed reaction medium is preferably 25 to 60%, more preferably 35 to 50%, by volume.

The most preferable combination of alkaline metal and ammonia or amine is that of lithium and ammonia.

According to the present invention, in a later stage of the reaction, a proton donor is added to the reaction mixture. The proton donor of the present invention is, for example, ammonium salts and amine salts, for example, those derived from mineral acids, such as halide, such as a fluoride and chloride, nitrates, and sulfates. Alcohol, for example, a lower alcohol such as methanol and ethanol, also may act as a proton donor. The amount of the proton donor is preferably 50 to 250 equivalent, more preferably 100 to 200 equivalent most preferably 150 to 180 equivalent, relative to the $1\alpha, 2\alpha$-epoxy-$\Delta^{4,6}$-3,24-dioxosteroid used.

To carry out the present process, first an alkaline metal or alkaline earth metal and a proton acceptor are dissolved in ammonia or amine in a liquid form, and to the solution, $1\alpha, 2\alpha$-epoxy-$\Delta^{4,6}$-3,24-dioxosteroid dissolved in an inert solvent is dropwise added. Then a proton donor is added to the reaction mixture. The reaction is preferably carried out with stirring, while eliminating moisture and/or oxygen from the reaction.

According to the present invention, $1\alpha, 3\beta, 24$-trihydroxy-$\Delta^5$-steroids are produced at a high yield, and thus the production cost of final product, $1\alpha$, 24-dihydroxyvitamin $D_3$ is reduced.

EXAMPLES

The present invention will now be further illustrated by, but is by no means limited to, the following examples and reference examples.

REFERENCE EXAMPLE 1

Production of $1\alpha, 3\beta$-dihydroxycholest-5-ene

First, 2.60 g (40 equivalent amount) of metal lithium was dissolved in 130 ml of liquid ammonia under a nitrogen atmosphere, and to the solution 3.60 g of $1\alpha, 2\alpha$-epoxycholesta-4,6-dien-3-one dissolved in 150 ml of tetrahydrofuran was dropwise added for 90 minutes, while maintaining a temperature of the reaction mixture at $-75°$ C. After 60 minutes had elapsed, 36 g (72 equivalent amount) of the total amount of ammonium chloride was added in ten portions at 10 minute intervals and stirring was continued until the lithium layer disappeared.

Next, after evaporating most of the ammonia from the reaction mixture at room temperature, water was added to the reaction mixture, which was then extracted with ethyl acetate. The extract was sequentially washed with 1 N hydrochloric acid, a saturated sodium bicarbonate aqueous solution, and a saturated sodium chloride aqueous solution. The mixture was dried over magnesium sulfate and concentrated to dryness. The residue was chromatographed on about ten amount of silica gel using benzene/acetone as a eluate to obtain $1\alpha, 3\beta$-dihydroxy-cholest-5-ene at a yield of 78%.

REFERENCE EXAMPLE 2

Production of $1\alpha, 3\beta, 24$-trihydroxycholest-5-ene

First, 2.79 g (55 equitrivalent amount) of metal lithium was dissolved in 130 ml of liquid ammonia in a nitrogen atmosphere, and to the solution 3.00 g of $1\alpha, 2\alpha$-epoxycholesta-4,6-dien-3,24-dione dissolved in 150 ml of tetrahydrofuran was dropwise added for 90 minutes, while maintaining the temperature of the reaction mixture at −75° C. Then 60 minutes later, 37.2 g (95 equivalent amount) of the total amount of ammonium chloride was added in ten portions at 10 minute intervals, and stirring was continued until the lithium layer disappeared.

Next after evaporating most of the ammonia from the reaction mixture at room temperature, the same procedure as described in Reference Example 1 was carried out to obtain 1α, 3β, 24-trihydroxycholest-5-ene at a yield of 60%, which was lower than that of the 1α, 3β-dihydroxy-cholest-5-ene in Reference Example 1.

An analysis of this product reveled that the product contained a substantial amount of dimer of 1α, 3β, 24-trihydroxycholest-5-ene.

EXAMPLE 1

Production of 1α, 3β, 24-trihydroxy-cholest-5-ene

First, 2.79 g (55 equivalent amount) of metal lithium and 3.4 g (10 equivalent amount) of lithium ethoxide were dissolved in 130 ml of liquid ammonia under a nitrogen atmosphere and to the solution, 3.00 g of 1α, 2α-epoxycholesta-4,6-dien-3,24-dione dissolved in 150 ml of tetrahydrofuran was dropwise added for 90 minutes while maintaining the temperature of the reaction mixture at −75° C. Then 60 minutes later, to the reaction mixture was added 37.2 g (95 equivalent amount) of ammonium chloride in ten portions at 10 minute intervals. Stirring was continued until the lithium layer disappeared.

Next, after evaporating most of the ammonia from the reaction mixture at room temperature, the same procedure as described in Reference Example 1 was carried out to obtain 1α, 3β, 24-trihydroxylcholest-5-ene at a yield of 79%.

A comparison between the product of Example 1 and that of Reference Example 2 by HPLC analysis revealed that the product of Example 1 essentially does not contain the dimer byproduct.

REFERENCE EXAMPLE 3

Production of 1α, 3β, 24-trihydroxycholest-5-ene

First, 1.80 g (35 equivalent amount) of metal lithium was dissolved in 130 ml of liquid ammonium under a nitrogen atmosphere and to the solution 3.00 g of 1α, 2α-epoxycholesta-4,6-dien-3,24- dione dissolved in 150 ml of tetrahydrofuran was dropwise added for 90 minutes while maintaining the temperature of the reaction mixture at −75° C. Then 60 minutes later, the temperature of the reaction mixture was increased to −34° C. for about 30 minutes and to the mixture was dropwise added 40.3 g (120 equivalent amount) of ethanol. Stirring was continued until the lithium layer floating as a liquid layer on the reaction mixture disappeared. Next, after evaporating most of the ammonia from the reaction mixture at room temperature, the same procedure as described in Reference Example 1 was carried out to obtain 1α, 3β, 24-trihydroxycholest-5-ene at a yield of 63%.

Reference Example 4

Production of 1α, 3β, 24-trihydroxycholest-5-ene

First 1.80 g (35 equivalent amount) of metal lithium and 40.3 g (120 equivalent amount) of ethanol were dissolved in 130 ml of liquid ammonia under a nitrogen atmosphere and to the solution 3.00 g of 1α, 2α-epoxycholesta-4,6-dien-3,24-dione dissolved in 50 ml of tetrahydrofuran was dropwise added for 90 minutes while maintaining the temperature of the reaction mixture at −75° C. Then 60 minutes later, the temperature of the reaction mixture was increased to −34° C. for about 30 minutes and stirring was continued until a lithium layer floating as a liquid layer on the reaction mixture disappeared.

Next, after evaporating most of the ammonia from the reaction mixture, the same procedure as described in Reference Example 1 was carried out to obtain 1α, 3β, 24-trihydroxycholest-5-ene at a yield of 20%. An HPLC analysis of the product revealed that the product contained a substantial amount of 1α, 3β, 24-trihydroxy-cholest-6-ene although there was very little formation of the dimer byproduct.

EXAMPLES 2 to 4

Production of 1α, 3β, 24-trihydroxycholest-5-ene

First, 1.8 g (35 equivalent amount) of metal lithium and an alkoxide (10 equivalent amount) shown in Table 1 was dissolved in 130 ml of liquid ammonia under a nitrogen atmosphere and to the solution 3.00 g of 1α, 2α-epoxycholesta-4,6-dien-3,24-dione dissolved in 150 ml tetrahydrofuran was dropwise added for 90 minutes while maintaining the temperature of the reaction mixture at −75° C. Then 60 minutes later, the temperature of the reaction mixture was increased to −34° C. for about 30 minutes. To the mixture was added dropwise 4.0 g (120 equivalent amount) of ethanol. Stirring was continued until the lithium layer floating as a liquid layer on the reaction mixture disappeared.

Next, after evaporating most of the ammonia from the reaction mixture at room temperature, the same procedure as described in Reference Example 1 was carried out to obtain 1α, 3β, 24-trihydroxycholest-5-ene at a yield shown in Table 1.

TABLE 1

| Example No. | Alkoxide | Yield (%) |
|---|---|---|
| 2 | Lithium ethoxide | 80 |
| 3 | Lithium n-butoxide | 79 |
| 4 | Sodium ethoxide | 85 |

As seen from Table 1, the addition of an alkoxide of primary alcohol having at least two carbon atoms with alkaline metal at an early stage of the reaction provides a yield significantly higher than those of the preceding Reference Examples.

REFERENCE EXAMPLE 5

Production of 1α, 3β, 24-trihydroxycholest-5-ene

First, 1.80 g (35 equivalent amount) of metal lithium was dissolved in 130 ml of liquid ammonia under a nitrogen atmosphere and to the solution 3.00 g of 1α, 2α-epoxycholesta-4,6-dien-3,24-dione dissolved in 150 ml of tetrahydrofuran was dropwise added for 90 minutes while maintaining the temperature of the mixture at −75° C. After completion of the addition, 3.4 g (10 equivalent amount) of lithium ethoxide was added to the reaction mixture. Then 60 minutes later the temperature of the reaction mixture was increased to −34° C. for about 30 minutes, 40.3 g (120 equivalent amount) of ethanol was dropwise added to the reaction mixture and stirring was continued until the lithium layer floating as a liquid layer on the reaction mixture disappeared.

Next, after evaporating most of the ammonia from the reaction mixture, the same procedure as described in Reference Example 1 was carried out to obtain 1α, 3β, 24-trihydroxycholest-5-ene at a yield of 60%. As seen from the result, the addition of lithium ethoxide as a proton acceptor at a later stage of the reaction did not increase the yield.

We claim:

1. A process for production of a 1α, 3β, 24-trihydroxy-$\Delta^5$-steroid represented by the formula (II)

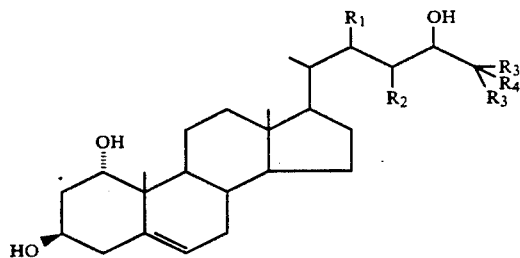

wherein $R_1$ and $R_2$, independently, represent a hydrogen atom, or $R_1$ and $R_2$, together form a single bond, $R_3$ represents an unsubstituted or halogen-substituted lower alkyl, and $R_4$ represents a hydrogen atom, hydroxy or a protected hydroxy, comprising the steps of:

(a) reacting a
1α, 2α-epoxy-$\Delta^{4,6}$3,24-dioxosteroid represented by the formula (I):

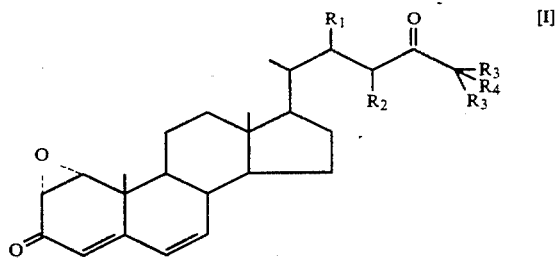

wherein $R_1$, $R_2$, $R_3$ and $R_4$ have the same meanings as defined for formula (II) with an alkaline metal or alkaline earth metal in the presence of a proton acceptor which is an alkaline metal alkoxide of a primary alcohol having at least two carbon atoms in a solvent comprising ammonia or amine; and thereafter (b) reacting the product of step (a) which contains an alkaline metal or alkaline earth metal in the presence of a proton donor.

* * * * *